United States Patent
Kim et al.

(10) Patent No.: US 9,926,585 B2
(45) Date of Patent: Mar. 27, 2018

(54) METHOD FOR PRODUCING A MINOR GINSENOSIDE USING A GINSENOSIDE GLYCOSIDASE

(71) Applicant: INTELLIGENT SYNTHETIC BIOLOGY CENTER, Daejeon (KR)

(72) Inventors: Sun Chang Kim, Daejeon (KR); Wan Taek Im, Gyeonggi-do (KR); Chang Hao Cui, Daejeon (KR)

(73) Assignee: INTELLIGENT SYNTHETIC BIOLOGY CENTER, Daejeon (KR)

(*) Notice: Subject to any disclaimer, the term of this patent is extended or adjusted under 35 U.S.C. 154(b) by 0 days.

(21) Appl. No.: 15/190,787

(22) Filed: Jun. 23, 2016

(65) Prior Publication Data
US 2017/0175159 A1    Jun. 22, 2017

(30) Foreign Application Priority Data
Dec. 18, 2015  (KR) .................. 10-2015-0181763

(51) Int. Cl.
| C12P 33/00 | (2006.01) |
| C12P 33/20 | (2006.01) |
| C12P 19/44 | (2006.01) |
| C12N 9/42  | (2006.01) |

(52) U.S. Cl.
CPC ............ *C12P 33/20* (2013.01); *C12N 9/2445* (2013.01); *C12P 19/44* (2013.01); *C12P 33/00* (2013.01); *C12Y 302/01021* (2013.01)

(58) Field of Classification Search
None
See application file for complete search history.

(56) References Cited

FOREIGN PATENT DOCUMENTS

KR    101340079 B1    1/2014

OTHER PUBLICATIONS

Machine translation of KR101340079 published Jan. 24, 2014.*
GenBank Accession No. WP_013585536, "beta-glucosidase [*Microbacterium testaceum*]" May 27, 2013, accessed Oct. 20, 2017.
Kim et al., "Bioconversion of major ginsenosides Rg1 to minor ginsenoside F1 using novel recombinant ginsenoside lydrolyzing glycosidase cloned from Sanguibacter keddieii and enzyme characterization," J. of Biotechnol., vol. 161, pp. 294-301, Jul. 2, 2012.

* cited by examiner

*Primary Examiner* — Rebecca E Prouty
(74) *Attorney, Agent, or Firm* — Gavrilovich, Dodd & Lindsey LLP

(57) ABSTRACT

Provided are a method of producing minor ginsenosides using a ginsenoside glycosidase protein derived from a *Microbacterium* sp. (*Microbacterium testaceum*) microorganism, and a composition including the protein for conversion into minor ginsenosides. The ginsenoside glycosidase exhibits very excellent activity of specifically hydrolyzing a sugar at the C-6 position of ginsenoside to convert the ginsenoside into in-vivo absorbable minor ginsenoside, thereby being very usefully applied to mass-production of ginsenoside.

3 Claims, 3 Drawing Sheets

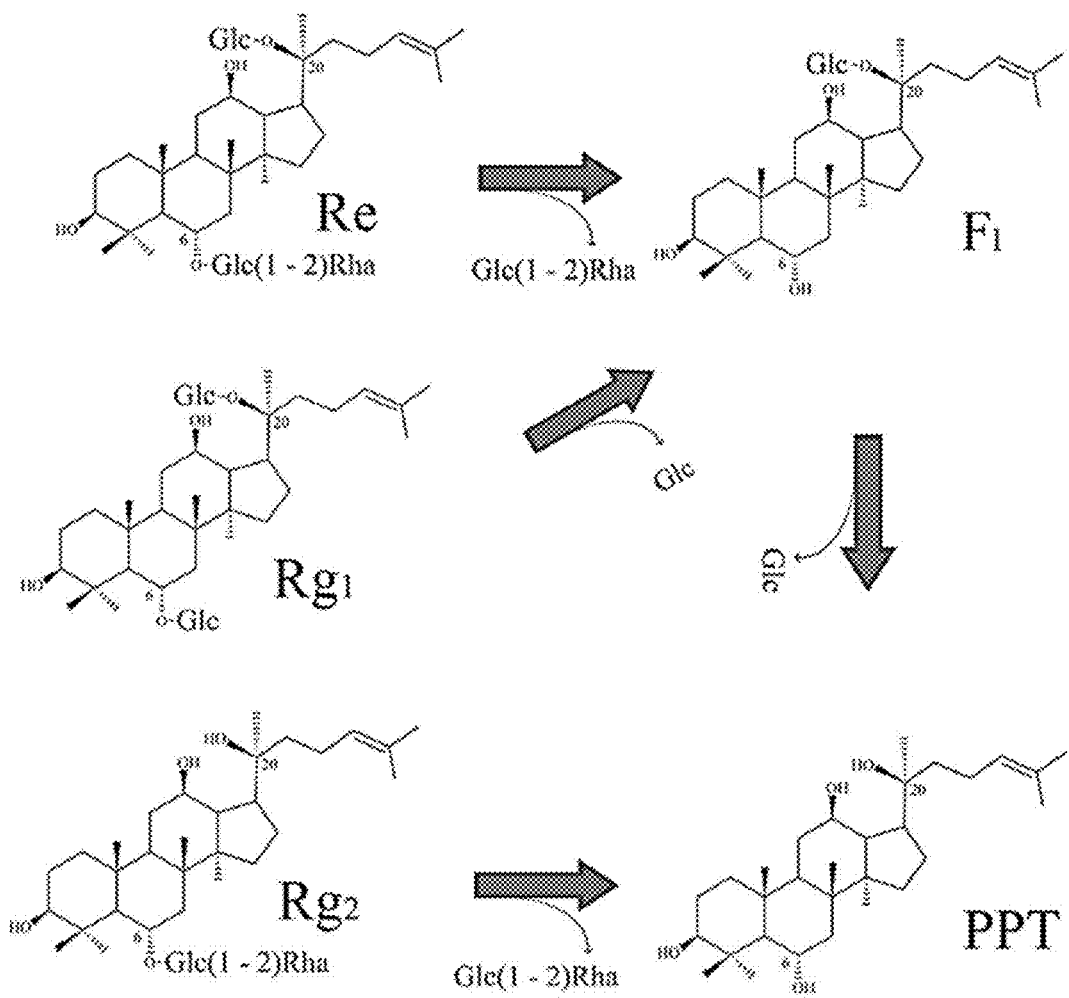
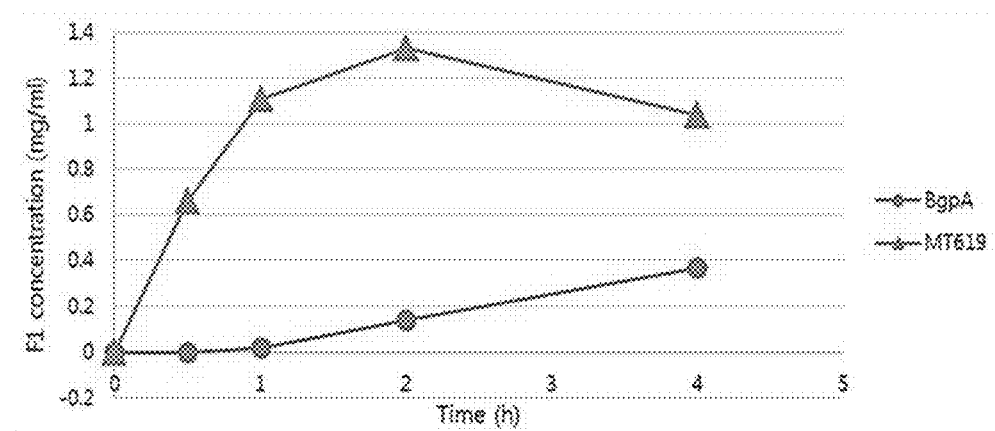
FIG. 6

METHOD FOR PRODUCING A MINOR GINSENOSIDE USING A GINSENOSIDE GLYCOSIDASE

CROSS REFERENCE TO RELATED APPLICATIONS

This application claims priority under 35 U.S.C. § 119 to Korean Patent Application No. 10-2015-0181763, filed Dec. 18, 2015, the disclosure of which is incorporated herein by reference.

BACKGROUND OF THE INVENTION

1. Field of the Invention

The present invention relates to a method of producing a minor ginsenoside using a ginsenoside glycosidase protein derived from a *Microbacterium* sp. microorganism, and a composition including the protein for conversion into a minor ginsenoside.

2. Description of the Related Art

Saponins, glycosides widely distributed in the plant kingdom, include diverse ring compounds formed by the non-sugar portion. Triterpene saponin, a saponin contained in *ginseng* or red *ginseng* as a major physiologically active ingredient, is named for distinguish with the other vegetable's saponin because of different chemical structure, called ginsenoside, which means *ginseng* glycoside.

Ginsenosides are classified into three groups based on their aglycone structure: Protopanaxadiol-type (PPD-type) ginsenosides, Protopanaxatriol-type (PPT-type) ginsenosides, and Oleanolic acid-type ginsenosides. These three groups are further classified based on the position and number of sugar moieties (aglycones) attached by a glycosidic bond at C-3, C-6, and C-20 positions of the rings in the chemical structure. PPD-type ginsenosides include $Rb_1$, $Rb_2$, $Rb_3$, Rc, Rd, Gypenoside (Gyp) XVII, Compound O, Compound Mc1, $F_2$, Compound Y, Compound Mc, $Rg_3$, $Rh_2$, and C-K. PPT-type ginsenosides include Re, $Rg_1$, Rf, $Rg_2$, $Rh_1$ and $F_1$.

In addition, major ginsenosides account for over 90% of total ginsenoside content in dry *ginseng*, but show a very low in-vivo absorption because of their large size of about 1,000 daltons. Therefore, in order to increase the efficacy of ginsenoside, it is required that major ginsenosides are converted into minor ginsenosides showing a relatively excellent absorption and efficacy. That is, deglycosylation of major ginsenosides for removing glucose, arabinose, rhamnose, xylose, etc. constituting sugars is required to show effective physiological activities in-vivo. The major ginsenosides include $Rg_1$, Re, $Rb_1$, $Rb_2$, Rc, Rd or the like, and the minor ginsenosides (rare ginsenosides) present in trace amounts include $F_2$, $Rg_3$, $Rh_1$, $Rh_2$, gypenoside (Gyp) XVII, gypenoside LXXV, Compound K, C-K, Compound Mc, Compound Mc1 or the like.

Rare ginsenoside $F_1$ is known to have efficacies of anti-aging and anti-oxidation, to protect HaCaT keratinocytes from UVB-induced cell apoptosis, and to have a skin whitening effect and an anti-cancer activity. Despite the usefulness of ginsenoside $F_1$, its pharmacological activities have been recently reported, since it was found in 1976, because ginsenoside $F_1$ is only present in the leaves of *ginseng* at relatively low concentrations, and thus it is difficult to obtain ginsenoside $F_1$ in an amount sufficient for a biological activity test.

For the production of minor ginsenoside $F_1$ present in *ginseng* in a small amount, a chemical decomposition, an enzymatic method, and a glycoside synthesis have been suggested, but these methods have limitations in mass-production, such as 1) many production steps required for the production process, 2) loss of desired compounds during processing, 3) use of inedible catalysts, or 4) low yield. In particular, with regard to the enzymatic method, there have many studies on use of coenzymes derived from various microorganisms and biotransformation of major ginsenosides of microorganisms. However, these methods are also not effective for mass-production, and have a problem of high production costs.

The production methods of $F_1$ reported until now include biological production of several mg of $F_1$, $Rh_1$, $Rg_2$ and $Rg_1$ from 0.5 g of a PPT-type mixture by using glycosidase or production of $F_1$ from $Rg_1$ by using β-glucosidase isolated from fungus. Further, as the latest technology of producing a large amount of ginsenoside $F_1$, it was reported that a large amount of $F_1$ is successfully produced in grams by using β-glucosidase derived from a *Terrabacter* sp. microorganism (Korean Patent NO. 10-1340079).

Accordingly, the present inventors have made many efforts to develop a method of producing minor ginsenosides which are present in a trace amount in plants such as *ginseng*, etc. As a result, they found that more excellent bioconversion of major ginsenosides into minor ginsenosides is catalyzed by ginsenoside glycosidase MT619 derived from a *Microbacterium* sp. strain than β-glucosidase derived from a *Terrabacter* sp., thereby completing the present invention.

SUMMARY OF THE INVENTION

An object of the present invention is to provide a method of producing a minor ginsenoside which is deglycosylated at the C-6 position, comprising:
treating one or more selected from the group consisting of a ginsenoside glycosidase protein having an amino acid sequence of SEQ ID NO: 1; a transformant introduced with a vector comprising a polynucleotide encoding the protein; and a culture of the transformant to a ginsenoside having a sugar at the C-6 position.

Another object of the present invention is to provide a composition for converting a ginsenoside having a sugar at the C-6 position into a minor ginsenoside which is deglycosylated at the C-6 position, comprising:
one or more selected from the group consisting of a ginsenoside glycosidase protein having an amino acid sequence of SEQ ID NO: 1; a transformant introduced with a vector comprising a polynucleotide encoding the protein; and a culture of the transformant.

Still another object of the present invention is to provide a ginsenoside glycosidase protein.

Still another object of the present invention is to provide a nucleotide encoding the protein, a vector including the nucleotide, and a transformant introduced with the vector.

BRIEF DESCRIPTION OF THE DRAWINGS

FIG. 5 shows conversion pathways of ginsenoside Re, $Rg_1$ and $Rg_2$ by recombinant MT619; and FIG. 6 shows $F_1$ production ability of recombinant MT619 (BgpA: glycosidase derived from *Terrabacter ginsenosidimutans*).

DETAILED DESCRIPTION OF THE PREFERRED EMBODIMENTS

Figure 1:
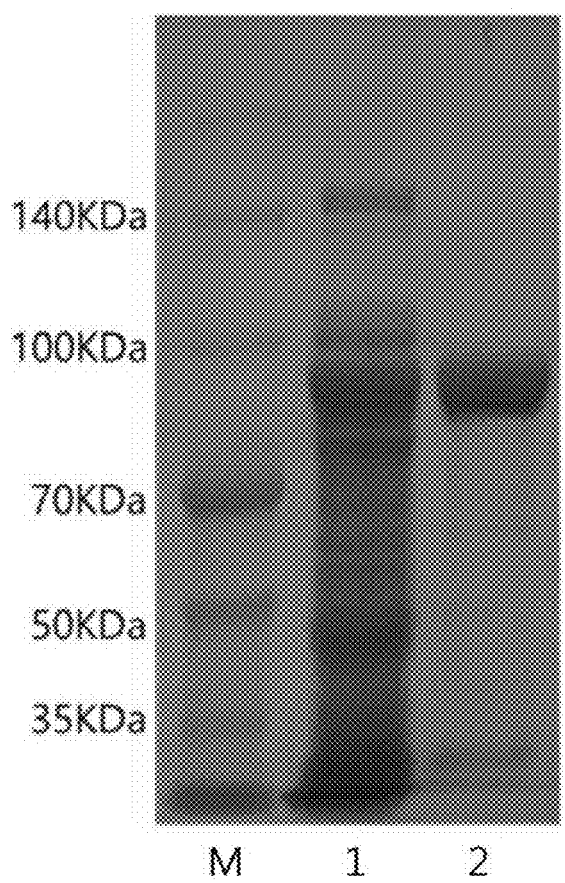
FIG. 1 shows the result of SDS-PAGE analysis of recombinant MT619 after being purified by a GST-bind agarose resin (M: size marker, Lane 1: crude extract having no protein expression, Lane 2: GST-MT619 after being purified by the GST-bind agarose resin)

To achieve the above objects, an aspect of the present invention provides a method of producing a minor ginsenoside which is deglycosylated at the C-6 position, comprising: treating one or more selected from the group consisting of a ginsenoside glycosidase protein having an amino acid sequence of SEQ ID NO: 1; a transformant introduced with a vector comprising a polynucleotide encoding the protein; and a culture of the transformant to a ginsenoside having a sugar at the C-6 position.

As used herein, the term "ginsenoside glycosidase" is an enzyme which catalyzes the hydrolysis of glycosidic bond, and specifically, an enzyme which specifically hydrolyzes a sugar at the C-6 position of ginsenoside. Although enzymes belong to the same glycosidase family, their enzymatic activities may differ such as glucosidase or cellulase. Therefore, it is necessary to investigate an appropriate enzyme having an activity of specifically hydrolyzing a sugar at the C-6 position of ginsenoside. Accordingly, the present inventors screened ginsenoside glycosidase having such activity, and they examined its function. With respect to the objects of the present invention, the ginsenoside glycosidase is not limited, as long as it is an enzyme hydrolyzing a sugar at the C-6 position of ginsenoside. Specifically, the ginsenoside glycosidase may have an amino acid sequence represented by SEQ ID NO: 1. In addition to the protein having the amino acid sequence represented by SEQ ID NO: 1, any protein is included in the present invention, as long as it includes an amino acid sequence having 70% or higher homology, specifically 80% or higher homology, more specifically 90% or higher homology, much more specifically 95% or higher homology, and most specifically 98% or higher homology with the sequence, and substantially has the activity of the ginsenoside glycosidase including the amino acid sequence of SEQ ID NO: 1. Further, it is apparent that any type of protein variants having a deletion, modification, substitution or addition of some sequence may be within the scope of the present invention, as long as the sequence having the homology is an amino acid sequence having a biological activity that is substantially identical or corresponding to that of the ginsenoside glycosidase.

The homology is intended to indicate the degree of similarity to the amino acid sequence of a wild type protein or a polynucleotide sequence encoding the same, and includes sequences having homology of the above percentage or higher with the amino acid sequence or polynucleotide sequence of the present invention. Homology comparisons may be conducted by eye or with the aid of readily available sequence comparison programs.

The ginsenoside glycosidase having the amino acid sequence represented by SEQ ID NO: 1 may be derived from a *Microbacterium* sp. microorganism, specifically, *Microbacterium testaceum*, and the ginsenoside glycosidase may be used herein interchangeably with MT619. The ginsenoside glycosidase has a beta-glucosidase (β-glucosidase) activity to degrade glucose, Glc(1→2)Glc, or rha (1→2)Glc, thereby catalyzing conversion of ginsenoside having a sugar attached at the C-6 position into minor ginsenosides, $F_1$ and PPT.

In an embodiment of the present invention, ginsenoside glycosidase having the amino acid sequence represented by SEQ ID NO: 1 was screened from *Microbacterium testaceum*, and the ginsenoside glycosidase was designated as MT619 (Example 1). A polynucleotide encoding MT619 includes a polynucleotide having a length of 1857 bp, and encodes a polypeptide consisting of 619 amino acids.

The ginsenoside glycosidase has a selective hydrolytic ability for the outer and inner glucoses, Glc(1→2)Glc or rha(1→2)Glc at the C-6 position of ginsenoside.

Figure 4:
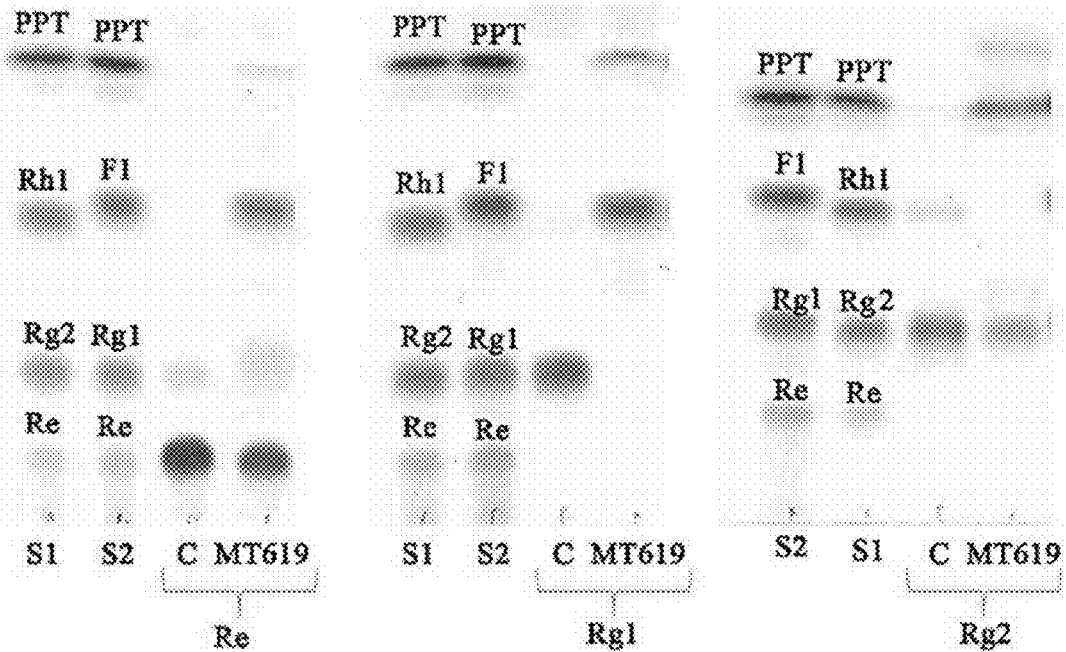
FIG. 4 shows the result of thin layer chromatography (TLC) for analyzing ginsenoside $F_1$ conversion by recombinant MT619 (S: ginsenoside standard)

In an embodiment of the present invention, conversion of ginsenoside $Rg_1$ into $F_1$ was confirmed, suggesting that the ginsenoside glycosidase of the present invention has a selective hydrolytic ability for glucoses at the C-6 position of ginsenoside, thereby preparing ginsenoside $F_1$ (FIG. 4).

The ginsenoside glycosidase protein of the present invention may catalyze conversion of ginsenoside having a sugar attached at the C-6 position into in-vivo absorbable, soluble minor ginsenosides, and this protein may be used under various temperature and pH conditions as long as its activity and stability are maintained. The protein may be used, together with one or more metals or chemical reagents selected from the group consisting of $CaCl_2$, $CoCl_2$, DTT, EDTA, KCl, $MgCl_2$, $MnCl_2$, NaCl, SDS and mercaptoethanol, but is not limited thereto.

In an embodiment of the present invention, effects of pH on activity and stability of MT619 were analyzed. As a result, MT619 showed stability in the range of pH 5 to 8.0, and specifically, the highest stability at pH 7.0 (Example 3-2, FIG. 2).

In another embodiment of the present invention, effects of temperature on activity and stability of MT619 were analyzed. As a result, MT619 showed high activity at 30~55° C., and optimum temperature was 45° C. Further, MT619 showed temperature stability at 0~45° C., and specifically, excellent stability at 0~30° C. (Example 3-3, FIG. 3).

In still another embodiment, effects of metals and other chemical reagents on MT619 activity were analyzed. As a result, the enzymatic activity was strongly inhibited in the presence of ions such as $Cu^{2+}$, $Co^{2+}$, $Hg^{2+}$, $Zn^{2+}$ or the like, but $Ca^{2+}$, $Na^+$ and $K^+$ did not greatly increase the enzymatic activity (Example 3-4, Table 1).

In still another embodiment of the present invention, substrate specificity of MT619 was analyzed. As a result, MT619 showed the highest substrate specificity for pNP-β-D-glucopyranoside, and also showed substrate specificity for o-NP-β-D-glucopyranoside (Example 4, Table 2).

Further, the ginsenoside glycosidase has much higher hydrolytic ability for glucoses at the C-6 position of ginsenoside than β-glucosidase derived from *Terrabacter* sp. microorganism which is known to produce a large amount of $F_1$, and therefore, the ginsenoside glycosidase may be usefully applied to mass-production of minor ginsenoside.

In an embodiment of the present invention, MT619 was used to evaluate an ability to produce $F_1$ from ginsenoside $Rg_1$. BgpA derived from *Terrabacter ginsenosidimutans* which is known to produce $F_1$ by using ginsenoside $Rg_1$ as a substrate was used as a comparative control group. As a result, it was found that MT619 has a very excellent ability to produce $F_1$ by using $Rg_1$ as a substrate. In detail, MT619 showed excellent production ability at 1 to 3 hrs and the highest production ability at 2 hrs after initiation of the reaction. At an enzyme concentration of 0.1 mg/ml, MT619 produced 1.3 mg of $F_1$ whereas BgpA produced 0.18 mg of $F_1$, indicating that MT619 showed 7 times higher production of $F_1$ than BgpA (FIG. 6).

These results suggest that ginsenoside glycosidase MT619 has very excellent hydrolytic ability for a sugar at the C-6 position of ginsenoside than the known ginsenoside glycosidase BgpA.

In the present invention, the ginsenoside having a sugar attached at the C-6 position may be a PPD (protopanazadiol)-type ginsenoside. The "PPT (protopanaxatriol)-type ginsenoside" is a dammarane-type saponin, and it means a PPT possessing —OH groups at the C-3, C-6, C-12, and C-20 positions, or a ginsenoside glycosylated at —OH groups of PPT. Example thereof includes ginsenoside Re, $Rg_1$, Rf, $F_1$, $Rg_2$, PPT or $Rh_1$. In particular, with respect to the objects of the present invention, the PPT-type ginsenoside includes all ginsenosides which may be converted into ginsenoside F1 or PPT by the activity of the ginsenoside glycosidase.

In an embodiment of the present invention, it was found that $Rg_1$ may be converted into $F_1$ by the activity of the ginsenoside glycosidase of the present invention (FIG. 4). The PPT-type ginsenoside may be specifically $Rg_1$, $Rh_1$, Re, $Rg_2$ and Rf, but is not limited thereto.

The PPT-type ginsenoside may be a ginsenoside in an isolated and purified form, or a ginsenoside contained in a powder or an extract of *ginseng* or red *ginseng*. That is, the powder or extract of *ginseng* or red *ginseng* containing ginsenoside may be directly used as a starting material to perform the method of the present invention. The *ginseng* used in the present invention includes the known various types of ginsengs, such as *Panax ginseng, P. quiquefolius, P. notoginseng, P. japonicus, P. trifolium, P. pseudoginseng*, and *P. vietnamensis*, but is not limited thereto.

As used herein, the term "minor ginsenoside" refers to an in-vivo absorbable minor ginsenoside which is produced by hydrolysis of a sugar at the C-6 position of hardly absorbable major ginsenoside. Specifically, the minor ginsenoside may be $F_1$ or PPT, but is not limited thereto.

In detail, the ginsenoside glycosidase has a selective hydrolytic ability for the C-6 position of ginsenoside $Rg_1$ or $Rh_1$ to hydrolyze one glucose moiety at the C-6 position, thereby converting ginsenoside $Rg_1$ or $Rh_1$ into ginsenoside $F_1$ or PPT, respectively.

Further, the ginsenoside glycosidase hydrolyzes rha (1→2)Glc at the C-6 position of ginsenoside Re or $Rg_2$, thereby converting ginsenoside Re or $Rg_2$ into ginsenoside $F_1$ or PPT, respectively. The ginsenoside glycosidase hydrolyzes Glc(1→2)Glc at the C-6 position of ginsenoside Rf, thereby converting ginsenoside Rf into ginsenoside $F_1$.

As used herein, the term "Glc(1→2)Glc" refers to a disaccharide linked by α or β bond between C-1 of glucose (Glc) and C-2 of the other glucose (Glc), and specifically, it may be a disaccharide linked by a bond between C-1 of glucose and C-2 of the other glucose, but is not limited thereto.

As used herein, the term "rha(1→2)Glc" refers to a disaccharide linked by α or β bond between C-1 of rhamnose (rha) and C-2 of glucose, and specifically, it may be a disaccharide linked by a bond between C-1 of rhamnose and C-2 of glucose, but is not limited thereto.

Specifically, the method of producing minor ginsenosides of the present invention includes one or more selected from the group consisting of conversion of ginsenoside $Rg_1$ into ginsenoside $F_1$, conversion of $Rh_1$ into PPT, conversion of Re into $F_1$, conversion of $Rg_2$ into PPT, conversion of Rf into $F_1$, and conversion of Rf into $F_1$, but is not limited thereto. The conversion activity of the ginsenoside glycosidase is given in FIG. 4.

The method of producing minor ginsenosides of the present invention may include the step of reacting ginsenoside having a sugar attached at the C-6 position with a transformant introduced with a vector including a nucleotide encoding the ginsenoside glycosidase protein or a culture broth of the transformant.

As used herein, the term "vector" is an expression vector capable of expressing a desired protein in a proper host cell, and it refers to a nucleic acid construct including essential regulatory elements operably linked to express a nucleic acid insert.

As used herein, the term "transformation" means introduction of DNA into a host cell so that DNA is replicable, either as an extra-chromosomal element or by chromosomal integration, that is, artificial genetic alteration by introducing a foreign DNA into a host cell.

The transformation method of the present invention may be performed by any transformation method, and it may be easily performed according to a general method known in the art.

The transformant introduced with the vector including the nucleotide encoding the ginsenoside glycosidase protein of the present invention, which is transformed by the method, refers to a transformant having an activity of converting a PPT-type ginsenoside into ginsenoside $F_1$, and preferably, a transformant having an activity of converting PPT-type ginsenoside Re or Rg1 into ginsenoside $F_1$, an activity of converting ginsenoside $Rh_1$ into PPT, an activity of converting Re into $F_1$, an activity of converting $Rg_2$ into PPT, or an activity of converting Rf into $F_1$, but is not limited thereto. Further, the transformant has an activity of converting a PPT-type ginsenoside into ginsenoside $F_1$, but is not limited thereto.

In the present invention, the host cell is not particularly limited, as long as it is able to express the nucleic acid of the present invention. Non-limiting examples of the host cell to be used in the present invention include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Saccharomyces cerevisiae* and *Schizosaccharomyces pombe*; animal cells, and insect cells.

Further, the culture obtained by culturing the transformant may be used to specifically hydrolyze a sugar at the C-6 position of the ginsenoside having a sugar attached at the C-6 position. In detail, the culture broth may be used to prepare ginsenoside $F_1$ or PPT by converting ginsenoside $Rg_1$, $Rh_1$, Re, $Rg_2$ or Rf.

As used herein, the term "cultureh" refers to a product obtained by culturing the transformant according to a known method of culturing a microorganism. The culture broth may include a culture supernatant or a cell lysate, and may include cells or not. The culture broth of the transformant introduced with the expression vector including the nucleotide encoding the ginsenoside glycosidase may have an activity of converting a PPT-type ginsenoside $Rg_1$, $Rh_1$, Re, $Rg_2$ or Rf into $F_1$ or PPT, but is not limited thereto.

Another aspect of the present invention provides a composition for converting a ginsenoside having a sugar at the C-6 position into a minor ginsenoside which is deglycosylated at the C-6 position, comprising: one or more selected from the group consisting of a ginsenoside glycosidase protein having an amino acid sequence of SEQ ID NO: 1; a transformant introduced with a vector comprising a polynucleotide encoding the protein; and a culture of the transformant.

The ginsenoside, the ginsenoside glycosidase protein, the minor ginsenoside, the transformant, and the culture broth are the same as described above.

The ginsenoside glycosidase protein has very high selective hydrolytic ability for the C-6 position of *ginseng* ginsenoside, thereby being usefully applied to mass-production of minor ginsenosides.

Still another aspect of the present invention provides the ginsenoside glycosidase protein having an amino acid sequence of SEQ ID NO: 1, the nucleotide encoding the protein, the vector including the nucleotide, and the transformant introduced with the vector.

The ginsenoside glycosidase protein, the polynucleotide encoding the protein, the vector including the polynucleotide, and the transformant introduced with the vector are the same as described above.

Specifically, the polynucleotide encoding the ginsenoside glycosidase protein may refer to a polynucleotide represented by SEQ ID NO: 2, but is not limited thereto. The nucleotide encoding the ginsenoside glycosidase is not limited, as long as it is a nucleotide encoding the protein having the ginsenoside glucosidase activity. Specifically, in addition to the nucleotide sequence represented by SEQ ID NO: 2, any nucleotide sequence is included, as long as it includes a sequence having 70% or higher homology, specifically 80% or higher homology, more specifically 90% or higher homology, much more specifically 95% or higher homology, and most specifically 98% or higher homology with the sequence and also encodes the protein substantially having the ginsenoside glycosidase activity. The homology is the same as described above.

Hereinafter, the present invention will be described in more detail with reference to Examples. However, these Examples are for illustrative purposes only, and the scope of the present invention is not intended to be limited by these Examples.

Example 1: Recombinant Expression Vector Including Novel Ginsenoside Glycosidase and Preparation of Transformed Microorganism In the present invention, in order to prepare a novel ginsenoside glycosidase capable of converting major ginsenosides into minor ginsenosides, ginsenoside glycosidase of SEQ ID NO: 1 was screened from *Microbacterium testaceum*, and designated as MT619. A base sequence (SEQ ID NO: 2) of MT619 was optimized by mutagenex (USA) for expression in *Corynebacterium glutamicum*.

Example 2: Production of Ginsenoside Glycosidase

In order to produce a large amount of ginsenoside glycosidase of Example 1, the transformed strain was inoculated in an Erlenmyer flask containing 100 ml of LB medium supplemented with ampicillin, and seed-cultured in a shaking incubator at 37° C. and 200 rpm until absorbance at 600 nm reached 0.6. Expressions of soluble proteins were examined at different temperatures (18, 22, 25, 30, 37° C.), and IPTG (isopropyl-beta-D-thiogalactoside) was added thereto at a final concentration of 0.1 mM to induce mass-expression of ginsenoside glycosidase of the present invention. When the strain entered a stationary phase, a culture broth of the strain was centrifuged at 6,000×g and 4° C. for 10 minutes, and then suspended in 100 mM sodium phosphate buffer (pH 7.0), followed by sonication of the cell solution using a sonicator. The cell lysate was centrifuged at 13,000×g and 4° C. for 15 minutes to obtain a supernatant of soluble ginsenoside glycosidase MT619. The supernatant was separated and purified, and MT619 was analyzed by SDS-PAGE.

As a result, the number of amino acids of the ginsenoside glycosidase MT61 was 619, and the amino acid sequence of MT619 was represented by SEQ ID NO: 1. Further, a molecular weight of GST-MT619 was found to be similar to about 94.4 kDa which was calculated from the amino acid sequence (FIG. 1).

Example 3: Characterization of Ginsenoside Glycosidase MT619 Enzyme

Example 3-1: Analysis of MT619 Activity 50 mM sodium phosphate buffer (pH 6.0) containing a substrate PNPG (p-nitrophenyl-β-D-glucopyranoside) was used to measure specific activity of the purified MT619 at 37° C. The reaction was terminated by treatment of 0.1 ml of 1 M $Na_2CO_3$ for 5 minutes, and release of p-nitrophenol was immediately measured at 405 nm. One unit of activity was defined as the amount of enzyme required to release 1 μmol of p-nitrophenol per minute. Specific activity is expressed as units per milligram of protein. Protein concentration was determined by bicinchoninic acid (BCA) assay (Pierce, Rockford, Ill.) using Bio-R of fetal bovine albumin (Sigma) as standard. All analysis methods were repeated in triplicate.

Example 3-2: Evaluation of Activity According to pH Change

In order to measure the effect of pH on the enzymatic activity of MT619, 2.0 mM pNPGlc (p-nitrophenyl-D-glucopyranoside; Sigma) was used as a substrate, and pH was adjusted using the following buffer (50 mM). pH range of 2 to 10: KCl—HCl (pH 2), glycine-HCl (pH 3), sodium acetate (pH 4 and pH 5), sodium phosphate (pH 6 and pH 7), Tris-HCl (pH 8 and pH 9) and glycine-sodium hydroxide (pH 10).

Further, the effect of pH on the enzymatic stability was measured. Enzyme was incubated in each of the above mentioned buffers at 4° C. for 24 hours, and then pNPGlc was analyzed in 50 mM potassium buffer to measure the enzymatic stability according to pH change. Residual activity was analyzed according to a standard analytical procedure, and the results are given in FIG. 2 as an activity percentage obtained at the optimum pH.

Figure 2:
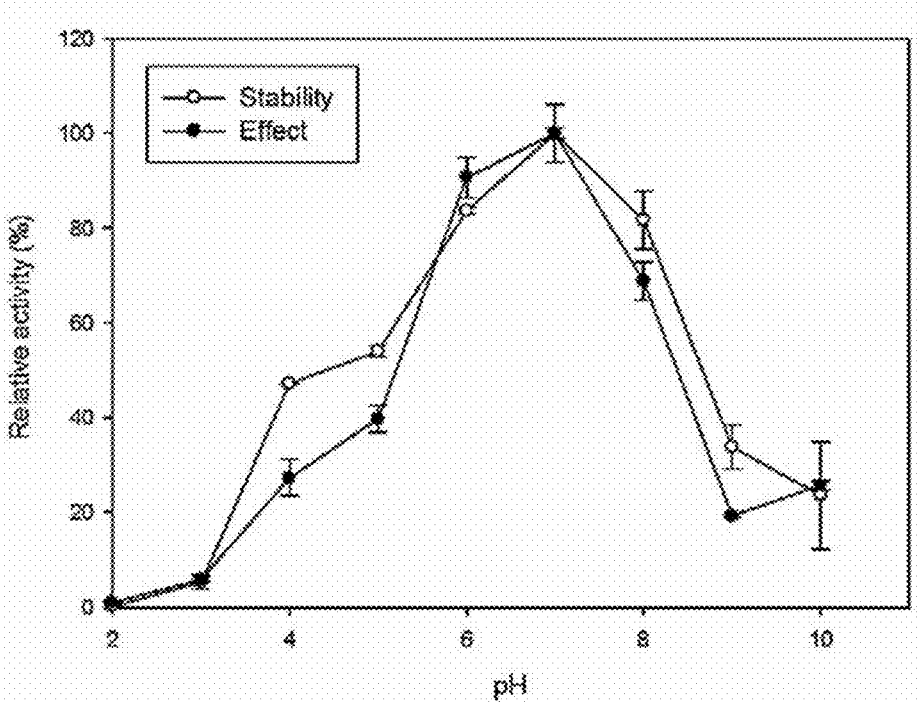
FIG. 2 shows effects of pH on activity and stability of the recombinant protein.

Consequently, as shown in FIG. 2, ginsenoside glycosidase MT619 showed activity and stability in the range of pH 6 to pH 8, and specifically, the highest activity and stability at pH 7.0. Further, the enzymatic activity and stability were rapidly decreased below pH 6.0 and above pH 8.0.

Example 3-3: Evaluation of Activity According to Temperature Change

In order to measure the effect of temperature on the enzymatic activity of MT619, 2.0 mM pNPGlc (p-nitrophenyl-3-Dglucopyranoside; Sigma) was used to analyze the temperature-dependent activity in the 50 mM potassium phosphate buffer at the optimum pH for 10 minutes while varying the temperature between 4 to 65° C.

Further, in order to measure the effect of temperature on the enzymatic stability of MT619, the equivalent amount of enzyme was incubated in 50 mM potassium phosphate buffer within the same temperature range for 30 minutes. In detail, the sample was cooled in ice for 10 minutes, and temperature stability analysis was performed by measuring the residual activity according to a standard analytical procedure, and the results are given in FIG. 3.

Figure 3:
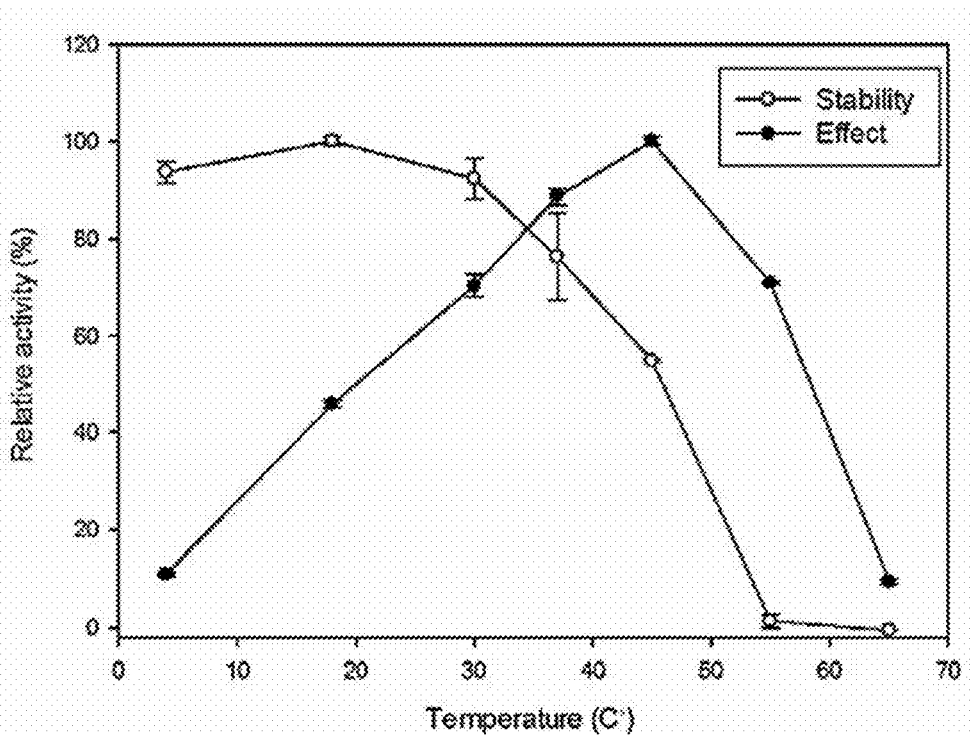
FIG. 3 shows effects of temperature on activity and stability of the recombinant protein.

Consequently, as shown in FIG. 3, ginsenoside glycosidase MT619 showed high activity at 30~55° C., and specifically, the highest activity at 45° C. Further, MT619 showed the temperature stability in the range of 0~45° C., and specifically, excellent stability at 0~30° C.

Example 3-4: Evaluation of Activity According to Metal and Chemical Reagent

In order to analyze the effects of metals and chemical reagents on the activity of ginsenoside glycosidase MT169, MT169 was incubated at 37° C. for 30 minutes, together with 10 mM of β-mercaptoethanol, $CaCl_2$, $COCl_2$, $CuCl_2$, dithiothreitol (DTT), EDTA, $HgCl_2$, KCl, $MgCl_2$, $MnCl_2$, NaCl, SDS or $ZnCl_2$, and pNPG was used as a substrate to measure the residual activity. The resulting value was represented as a percentage to the obtained activity upon lack of the compounds, and given in the following Table 1.

TABLE 1

| No. | | Relative activity (%) |
|---|---|---|
| 1 | Beta-Mercaptoethanol | 94 ± 2 |
| 2 | $CaCl_2$ | 132.8 ± 2.4 |
| 3 | $CoCl_2$ | 17.9 ± 0.5 |
| 4 | $CuCl_2$ | ND |
| 5 | DTT | 79.6 ± 1.6 |
| 6 | EDTA | 80.9 ± 2.3 |
| 7 | $HgCl_2$ | ND |
| 8 | KCl | 95.3 ± 1.1 |
| 9 | $MgCl_2$ | 112.7 ± 4.1 |
| 10 | $MnCl_2$ | 59.9 ± 2.6 |
| 11 | Nacl | 128.1 ± 3.7 |
| 12 | SDS | 80.6 ± 6.1 |
| 13 | $ZnCl_2$ | ND |
| 14 | Control | 100 ± 1.8 |

Consequently, as shown in Table 1, it was found that the enzymatic activity of ginsenoside glycosidase MT619 was strongly inhibited in the presence of ions such as $Cu^{2+}$, $Co^{2+}$, $Hg^{2+}$, $Zn^{2+}$ or the like, but the enzymatic activity was not greatly increased by $Ca^{2+}$, $Na^+$ and $K^+$.

Example 4: Analysis of Substrate Specificity of MT619

In order to analyze substrate specificity of MT169, 2.0 mM chromogenic O-nitrophenyl (ONP) and p-nitrophenyl (PNP) were used as substrates, and measured at 37° C. for 5 minutes. 1 activity unit was defined as the release of 1 μmol of o-nitrophenol or p-nitrophenol per minute. Substrates used for analysis were pNP-α-L-arabinofuranoside, pNP-β-L-arabinopyranoside, pNP-α-L-D-fucopyranoside, pNP-α-L-rhamnopyranoside, pNP-α-D-glucopyranoside, pNP-α-D-mannopyranoside, pNP-β-D-galactopyranoside, oNP-β-D-glucopyranoside, pNP-β-D-fucopyranoside, pNP-β-D-xylopyranoside, pNP-β-L-arabinofuranoside, oNP-β-D-fucopyranoside, oNP-α-D-galactopyranoside, and pNP-β-D-glucopyranoside, which were purchased from Sigma.

TABLE 2

| | Substrate | Relative activity (%) MT619 |
|---|---|---|
| 1 | pNP-α-L-arabinofuranoside | ND |
| 2 | pNP-α-L-arabinopyranoside | ND |
| 3 | pNP-α-L-D-fucopyranoside | ND |
| 4 | pNP-α-L-rhamnopyranoside | ND |
| 5 | pNP-α-D-glucopyranoside | ND |
| 6 | pNP-α-D-mannopyranoside | ND |
| 7 | pNP-β-D-glactopyranoside | ND |
| 8 | oNP-β-glucopyranoside | 28.7 ± 2.1 |
| 9 | pNP-β-D-fucopyranoside | ND |
| 10 | pNP-β-D-xylopyranoside | ND |
| 11 | pNP-β-L-arabinopyranoside | ND |
| 12 | oNP-β-D-fucopyranoside | ND |
| 13 | oNP-α-D-galactopyranoside | ND |
| C | pNP-β-D-glucopyranoside | 100 ± 1.2 | a: final substrate concentration 2.0 mM
b: relative to enzymatic activity for pNP-β-D-glucopyranoside Consequently, as shown in Table 2, ginsenoside glycosidase MT619 showed the highest substrate specificity for pNP-β-D-glucopyranoside, and also showed substrate specificity for o-NP-β-D-glucopyranoside. Ginsenoside glycosidase MT619 showed no substrate specificity for other substrates.

Example 5: Evaluation of Ginsenoside Conversion Ability of MT619

In order to analyze the specificity and selectivity of the enzyme for the hydrolysis of a sugar attached at the C-6 position of ginsenoside, ginsenoside Re, $Rg_1$ and $Rg_2$ were used as the substrates.

2.0 mg/ml of MT619 in 50 mM sodium phosphate buffer (pH 7.0) was reacted with each 2.0 mg/ml of the three substrates in 50 mM sodium phosphate (pH 6.0) at an equal volume at 37° C. In order to measure cleavage activity of MT619, the samples were collected at 1.5 hr after reaction, and an equal volume of water-saturated butanol was added to stop the reaction. The n-butanol fraction was evaporated to dryness, and residual material was dissolved in $CH_3OH$ and then examined by thin layer chromatography (TLC), and the results are given in FIG. 4.

Consequently, as shown in Table 4, ginsenoside Re and $Rg_1$ were found to be converted into ginsenoside $F_1$. These results indicate that ginsenoside $Rg_1$ is converted into ginsenoside $F_1$ by cleavage of the sugar at the C-6 position (FIG. 5).

These results support that ginsenoside glycosidase of the present invention represented by SEQ ID NO: 1 efficiently converts minor saponin, thereby producing soluble saponin ginsenoside $F_1$.

Example 6: Evaluation of F1 Production Ability of MT619

In order to evaluate production ability of MT619 to produce $F_1$ by using $Rg_1$ as a substrate, its $F_1$ production ability was compared with that of ginsenoside glucosidase derived from *Microbacterium testaceum*.

BgpA derived from *Terrabacter ginsenosidimutans*, which is known to produce $F_1$ by using ginsenoside $Rg_1$ as a substrate, was used as a comparative control group.

Consequently, as shown in FIG. 6, MT619 at a pure enzyme concentration of 0.1 mg/ml showed very excellent ability to produce $F_1$ by using $Rg_1$ (2.0 mg/ml) as a substrate.

MT619 rapidly produced $F_1$ from the beginning of the reaction, whereas BgpA showed low $F_1$ production ability at the beginning of the reaction. MT619 showed excellent production ability at 1 to 3 hrs, and specifically, the highest production ability at 2 hrs after initiation of the reaction. MT619 produced 1.3 mg of $F_1$ whereas BgpA produced 0.18 mg of $F_1$, indicating that MT619 showed 7 times higher production of $F_1$ than BgpA.

These results suggest that ginsenoside glycosidase MT619 shows very excellent hydrolytic ability specific to a sugar at the C-6 position of ginsenoside, compared to the known ginsenoside glycosidase BgpA.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

The present invention relates to a method of producing a minor ginsenoside using a ginsenoside glycosidase protein derived from a *Microbacterium* sp. (*Microbacterium testaceum*) microorganism, and a composition including the protein for conversion into a minor ginsenoside. The ginsenoside glycosidase exhibits very excellent activity of specifically hydrolyzing a sugar at the C-6 position of ginsenoside to convert the ginsenoside into in-vivo absorbable minor ginsenoside, thereby being very usefully applied to mass-production of ginsenoside.

What is claimed is:

1. A method of producing a minor ginsenoside which is deglycosylated at the C-6 position, comprising:
   treating a ginsenoside having a sugar at the C-6 position with a ginsenoside glycosidase protein consisting of the amino acid sequence of SEQ ID NO:1, wherein the ginsenoside having the sugar at the C-6 position is one or more ginsenosides selected from the group consisting of $Rg_1$, $Rh_1$, Re and $Rg_2$, and wherein the sugar is glucose or rha(1→2)Glc, wherein the ginsenoside glycosidase protein deglycosylates the ginsenoside at the C-6 position.

2. The method of claim 1, wherein the method comprises one or more selected from the group consisting of conversion of $Rg_1$ into $F_1$, conversion of Re into $F_1$, and conversion of $Rg_2$ into PPT.

3. The method of claim 1, wherein the deglycosylation is performed at pH 5 to pH 8.5 or at a temperature of 10° C. to 50° C.

* * * * *

SEQUENCE LISTING

```
<160> NUMBER OF SEQ ID NOS: 2

<210> SEQ ID NO 1
<211> LENGTH: 619
<212> TYPE: PRT
<213> ORGANISM: Microbacterium testaceum

<400> SEQUENCE: 1

Met Thr His Ala Arg Phe Leu Thr Ala Pro Asp Gly Thr Arg Phe Arg
1               5                   10                  15

Asp Leu Asn Gly Asn Gly Val Met Asp Pro Tyr Glu Asn Pro Ala Leu
            20                  25                  30

Ser Val Glu Glu Arg Thr Asp Asp Leu Val Ser Arg Leu Ser Leu Glu
        35                  40                  45

Glu Lys Val Gly Leu Met Phe Gln Thr Val Ile Glu Val Gly Asp Glu
    50                  55                  60

Gly Glu Leu Leu Glu Ala Pro Gly Lys Ile Ser Lys Ser Pro Thr Thr
65                  70                  75                  80

Thr Val Val Val Gly Lys His Met Asn His Phe Asn Val His Ala Ile
                85                  90                  95

Arg Thr Ala Arg Gln Ala Ala Thr Trp Asn Asn Asn Leu Gln Ala Leu
            100                 105                 110

Ala Glu Thr Thr Pro His Gly Ile Pro Val Thr Ile Ser Thr Asp Pro
        115                 120                 125

Arg His Ala Phe Val Glu Asn Thr Gly Val Ala Phe Ser Ala Gly Pro
    130                 135                 140

Phe Ser Gln Trp Pro Glu Gly Leu Gly Leu Ala Ala Leu Asp Asp Val
145                 150                 155                 160

Asp Thr Val Arg Glu Phe Ala Glu Val Ala Arg Arg Glu Tyr Val Ala
                165                 170                 175

Val Gly Ile Arg Ala Ala Leu His Pro Gln Ile Asp Leu Ala Thr Glu
            180                 185                 190

Pro Arg Trp Gly Arg Gln Ala Gln Thr Leu Gly Gln Asp Ala Ala Arg
        195                 200                 205

Val Thr Glu Phe Thr Ala Ala Tyr Leu Gln Gly Phe Gln Gly Asp Glu
    210                 215                 220

Leu Gly Pro Asp Ser Val Ala Cys Thr Thr Lys His Phe Pro Gly Gly
225                 230                 235                 240

Gly Pro Gln Leu Asp Gly Glu Asp Ala His Phe Pro Tyr Gly Arg Glu
```

```
                    245                 250                 255
Gln Val Tyr Pro Gly Gly Met Phe Asp Tyr His Leu Glu Pro Phe Arg
                260                 265                 270

Glu Ala Ile Arg Cys Gly Thr Ala Gly Met Met Pro Tyr Tyr Gly Met
            275                 280                 285

Pro Val Gly Leu Glu Val Asp Gly Leu Pro Ile Glu Glu Val Gly Phe
        290                 295                 300

Gly Tyr Asn Arg Gln Ile Ile Thr Gly Leu Leu Arg Glu Gln Leu Gly
305                 310                 315                 320

Tyr Asp Gly Val Val Thr Asp Trp Glu Leu Val Asn Asp Asn His
                325                 330                 335

Val Gly Asp Gln Val Leu Pro Ala Arg Ala Trp Gly Val Glu His Leu
                340                 345                 350

Ser Ala Val Glu Arg Met Glu Lys Ile Leu Asp Ala Gly Ser Asp Gln
            355                 360                 365

Phe Gly Gly Glu Glu Cys Val Glu Met Leu Val Asp Leu Val Arg Ala
        370                 375                 380

Gly Arg Val Ser Glu Glu Arg Ile Asp Glu Ser Val Arg Arg Leu Leu
385                 390                 395                 400

Arg Val Lys Phe Gln Leu Gly Leu Phe Asp Pro Tyr Val Asp Val
                405                 410                 415

Asp Glu Ala Glu Arg Ile Val Gly Asn Ala Glu Phe Arg Ala Leu Gly
            420                 425                 430

Glu Arg Ala Gln Ala His Ser Leu Thr Val Leu Val Asn Glu Gly Asp
        435                 440                 445

Val Leu Pro Leu Arg Pro Ala Gly Ala Val Tyr Ile Glu Gly Phe Arg
450                 455                 460

Pro Asp Asp Val Ala Glu Leu Gly Arg Val Val Thr Asp Pro Ala Glu
465                 470                 475                 480

Ala Asp Leu Ala Ile Val Arg Ile Gly Ala Pro Phe Asp Pro Arg Asp
                485                 490                 495

Asp Leu Phe Leu Glu Ala Trp Phe His Gln Gly Ser Leu Glu Phe Ala
            500                 505                 510

Pro Gly Leu Val Tyr Arg Leu Gln Gln Ile Ala Ala Ser Cys Pro Leu
        515                 520                 525

Ile Leu Val Val Asn Leu Asp Arg Pro Ala Ile Leu Thr Pro Phe Val
        530                 535                 540

Gly His Ala Ala Ala Ile Val Ala Asp Tyr Gly Ser Ser Ser Ala Ala
545                 550                 555                 560

Val Leu Asp Ala Leu Thr Gly Arg Val Pro Pro Arg Gly Arg Leu Pro
                565                 570                 575

Ile Glu Ile Pro Arg Ser Met Asp Ala Val Arg Ser Ser Arg Glu Asp
            580                 585                 590

Val Pro Ser Asp Thr Gly Asp Pro Val Phe Pro Val His His Gly Val
        595                 600                 605

Glu Leu Lys Val Ser Thr Gly Ala Gln Arg Gly
        610                 615

<210> SEQ ID NO 2
<211> LENGTH: 1860
<212> TYPE: DNA
<213> ORGANISM: Artificial Sequence
<220> FEATURE:
<223> OTHER INFORMATION: MT619
```

```
<400> SEQUENCE: 2
atgacccacg ctcgcttcct gaccgctcct gacggcacgc gcttccgtga tctcaacggt      60
aatggcgtca tggacccata cgagaaccca gccctctctg ttgaggagcg taccgacgac     120
ttggttagcc gcctctccct cgaagagaaa gtaggactta tgttccagac tgtaattgaa     180
gtcggtgacg aaggtgagct gttggaagca ccgggaaaaa tcagcaagtc cccgaccact     240
acagttgtcg tcgcaagca tatgaaccac ttcaacgtgc atgctatccg cactgctcgc     300
caggctgcca cctggaataa caacctccaa gccctggcgg aaacaacccc ccacggtatc     360
ccggtgacaa tctccactga tccacgacac gctttcgtgg agaatactgg cgtagctttc     420
tccgcaggcc cattctcgca gtggccagaa ggccttggcc tggcagcctt ggacgatgtg     480
gataccgtcc gtgaatttgc agaagtcgcg cgccgtgagt atgtcgcagt tggcattcgc     540
gccgctttgc atcctcagat tgatcttgca accgaacctc gctggggccg ccaggctcaa     600 accccttggtc aggatgcggc acgtgtgact gaattcaccg ctgcctactt gcagggcttc     660
caaggcgacg agcttggtcc agattcggta gcttgcacca ccaaacactt tcctggaggc     720
ggccctcaac tcgacggcga agatgcgcat ttcccctatg ccgcgagca agtgtaccca     780 ggtggtatgt tgattatca tctcgagccg tttcgcgaag ctatccgttg cggtaccgct     840
ggcatgatgc catattacgg catgcctgtt ggtctcgagg ttgatggact ccccatcgaa     900
gaggtaggtt tcggatacaa tcgccaaatc attacggac tgcttcgtga acaactcggc     960
tatgatggag ttgtcgtgac cgactgggaa ctcgtaaacg ataaccacgt cggcgatcag    1020
gttctcccgg cacgcgcgtg gggagtgaa cacctgtcag cagtagaacg tatggaaaag    1080
atcctggatg cgggctcaga tcagttcggc ggtgaggagt gcgtcgaaat gttggtggat    1140
ctggtccgtg caggtcgcgt aagcgaagag cgcattgacg agagcgttcg tcgcctcttg    1200
cgtgtaaagt ttcaactcgg tctgttcgac gatccctacg tcgatgtgga tgaggcggag    1260
cgaatcgtag gaaacgcaga gttccgtgcg ctcggcgagc gcgcccaggc acattccctc    1320
accgtgctgg ttaacgaagg cgacgtgttg cccctgcgcc ccgcaggcgc tgtctatatc    1380
gagggctttc gtcccgatga tgtggctgaa ctcggccgtg ttgttaccga ccctgccgag    1440
gcggacctcg caatcgtacg catcggcgca ccgttcgatc cccgcgatga tctgttcctg    1500
gaggcatggt tccatcaggg ttccttggaa tttgccccag gccttgtcta tcgcctgcaa    1560
cagatcgcgg cgtcctgccc attgatcctg gtcgtcaatc tcgaccgtcc ggctatcctg    1620
acgcctttcg ttggccacgc tgccgcaatc gtcgcagact acggctcttc gagcgctgcg    1680
gtcctggacg cattgaccgg tcgtgtgcct ccacgcggac gcctgcccat tgaaatccca    1740
cgttccatgg acgcggtgcg ctcctcgcgt gaagatgttc cctcagacac tggagatcct    1800
gttttccctg ttcaccacgg tgttgaattg aaagtttcga cgggtgcaca gcgcggataa    1860
```